United States Patent [19]

Walton et al.

[11] Patent Number: 4,627,849

[45] Date of Patent: Dec. 9, 1986

[54] TAMPON

[75] Inventors: Richard R. Walton, Boston; Richard C. Walton, East Orleans; George E. Munchbach, Roslindale, all of Mass.; Robert W. Young, New York, N.Y.

[73] Assignee: Kimberly-Clark Corporation, Neenah, Wis.

[21] Appl. No.: 754,669

[22] Filed: Jul. 11, 1985

Related U.S. Application Data

[63] Continuation of Ser. No. 393,543, Jun. 30, 1982, abandoned.

[51] Int. Cl.$^4$ .............................................. A61F 13/16
[52] U.S. Cl. ................................. 604/379; 604/385 R; 604/380; 604/904
[58] Field of Search ............... 604/904, 385, 375, 377, 604/379, 380

[56] References Cited

U.S. PATENT DOCUMENTS

| | | |
|---|---|---|
| 1,964,911 | 7/1934 | Haas . |
| 2,058,275 | 10/1936 | Voss . |
| 2,112,021 | 3/1938 | Harris ................................. 604/379 |
| 2,286,817 | 6/1942 | Knight ................................ 604/379 |
| 2,437,265 | 3/1948 | Manning . |
| 2,444,528 | 7/1948 | Popper et al. ...................... 604/904 |
| 2,499,414 | 3/1950 | Rabell ................................. 604/904 |
| 2,761,449 | 9/1956 | Bletzinger . |
| 2,761,490 | 9/1956 | Walton . |
| 2,765,513 | 10/1956 | Walton . |
| 2,765,514 | 10/1956 | Walton . |
| 2,815,756 | 12/1957 | Graham, Jr. ....................... 604/904 |
| 2,915,109 | 12/1959 | Walton . |
| 3,063,453 | 11/1962 | Brecht ................................. 604/904 |
| 3,220,056 | 11/1965 | Walton . |
| 3,220,057 | 11/1965 | Walton . |
| 3,260,778 | 7/1966 | Walton . |
| 3,359,981 | 12/1967 | Hochstrasser ..................... 604/379 |
| 3,426,405 | 2/1969 | Walton . |
| 3,593,715 | 7/1971 | Merr ................................... 604/904 |
| 3,710,793 | 1/1973 | Glassman .......................... 604/904 |
| 3,810,280 | 5/1974 | Walton et al. . |
| 3,811,445 | 5/1974 | Dostal . |
| 3,869,768 | 3/1975 | Walton et al. . |
| 3,975,806 | 8/1976 | Walton et al. . |
| 4,142,278 | 3/1979 | Walton et al. . |
| 4,200,101 | 4/1980 | Glassman .......................... 604/904 |
| 4,217,900 | 8/1980 | Wiegner et al. ................... 604/904 |
| 4,274,412 | 6/1981 | Austin ................................. 604/904 |
| 4,296,234 | 10/1981 | Mindt et al. ....................... 604/375 |
| 4,335,720 | 6/1982 | Glassman .......................... 604/904 |
| 4,335,721 | 6/1982 | Matthews .......................... 604/904 |
| 4,340,556 | 7/1982 | Ciencewicki ..................... 604/368 |
| 4,341,214 | 7/1982 | Fries et al. ......................... 604/904 |

FOREIGN PATENT DOCUMENTS 537113 11/1939 United Kingdom .

Primary Examiner—C. Fred Rosenbaum
Assistant Examiner—S. Vinyard

[57] ABSTRACT

The exterior of a compressed tampon, e.g. for absorbing menstrual discharge, is formed from a bat of substantially aligned absorbent fibers that have been preshortened in a microundulated state as a result of longitudinal compressive pretreatment. The preshortening, generally more than 20% of original length of the fibers, is selected to permit substantial recovery of original dimension, there being at least 10 of the microundulations per inch prior to incorporation in the tampon. The microundulations are shape-retentive (in the dry state) and reside with the sides of adjacent microundulations close together. Because of the pretreated state, the absorbent fibers have stored mechanical energy in a predetermined selected direction within the final tampon. They are highly moisture sensitive, responsive to small amounts of liquid to cause release of the mechanical energy and expansion in the given direction to cause rapid expansion of the exterior of the tampon. One preferred tampon has such a pretreated outer layer and an inner core of nontreated tampon material, though many other constructions are possible. In this preferred tampon the pretreated outer layer serves as a high-speed transfer member to uniformly distribute the fluids about the core to produce high rate of expansion, high total expansion and improved absorbency.

33 Claims, 31 Drawing Figures

I SMALL DROP

II LARGE DROP, X DIRECTION

III LARGE DROP, Y DIRECTION

UNCOMPACTED
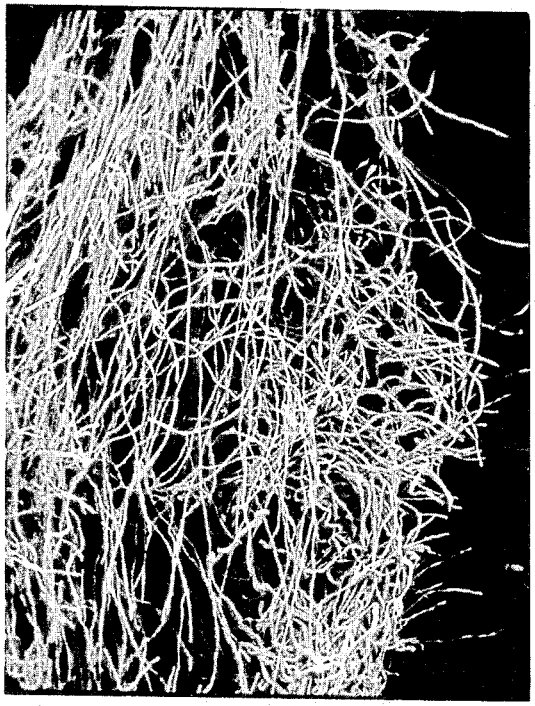
FIG 14
BLEACHED
BLEND
MAGNIFICATION 30X
COMPACTED-COARSE
COMPACTED-FINE

S.I. RAYON

MAGNIFICATION 50X

UNCOMPACTED

COMPACTED

RAYON TOW

MAGNIFICATION 50X

UNCOMPACTED

COMPACTED

TAMPON

This is a continuation of application Ser. No. 393,543, filed June 30, 1982, now abandoned.

BACKGROUND

This invention relates to catamenial tampons and the like.

The menstrual discharge (comprising endometrial cells, secretions and blood), is intermittent and takes place over hours and days. The blood and other matter exude following the line of gravity. Sometimes the flow is light, sometimes heavy. The purpose of a tampon is not necessarily to plug up this discharge, but rather it is to prevent leakage of this discharge by absorption of the liquid into the body of the removable tampon. Because blood and other matter tend to coagulate, clog and mat up the fibers in present tampons, damming can occur that prevents access of the fluid into the tampon, encouraging vertical by-pass leakage before the normal useful life of the tampon has been used. Such early leaking may occur down the sides or string and especially next to a damming area. Bypass leakage can also occur due to slow response of the tampon to expand upon first contact with moisture after insertion of the tampon.

Improved tampon constructions are desirable for decreasing the risk of early leakage, for increasing the efficiency of use of tampon fibers, and for decreasing the cost of production and increasing the facility with which tampons are made.

SUMMARY OF THE INVENTION

The present invention employs a longitudinal compressive pretreatment (facially confined) of the constituent fiber bat in the dry state to produce microundulations with ridges of the undulations tightly pressed together. This treatment animates and energizes in unison the outer fibers of the tampon in response to fluid contacting the tampon surface to maintain open passageways for the menstrual discharge to seek its way to full saturation of the tampon fiber mass. The activated fiber movement assists absorption of the liquid until the total fiber mass has been saturated. The dangers of clogging, damming and unused white areas of the tampon are reduced considerably which should reduce leakage problems.

Furthermore, a concerted movement of the fibers of the bat in a predetermined direction, though the fibers are not bonded to one another, is produced by the compressed microundulations. This concerted movement can expand the surface of the tampon in an action somewhat similar to the expansion of an accordion, with force attributable to the mechanical energy that was stored in the individual fibers by the pretreatment. The effect is concentrated in the direction of pretreatment and therefore can provide substantial growth, as may be desired, in a desired direction of the formed tampon, e.g. for radial expansion to prevent early leakage, or to enable axial growth in a tampon normally not having this capability.

The invention also enables avoidance of the hard-end problem that often confronts tampon designs of the type that employ compression in the axial direction during the making of the tampon. This is a result of the uniform pretreatment of the bat, and the ability of the treated material to retain its capability to expand (e.g. resists fusing) even after having been subjected to molding temperature and pressure.

Furthermore, the invention enables novel two-part tampon construction in which originally exposed cut-edges of the inner part are essentially protected by rapid enveloping motion of the expanding microcreped outer layer.

In accordance with one aspect of the invention, a compressed tampon for absorbing menstrual discharge is provided comprising, at its exterior at least, a bat of absorbent fibers in a preshortened state as a result of longitudinal compressive treatment, this bat being preshortened in a predetermined direction at least about 20% of original length, to a degree permitting substantial recovery of original dimension, there being at least 10 microundulations of the bat per inch prior to incorporation in the tampon, the microundulations being shape-retentive when dry and prior to incorporation in the tampon being compressed together so that the sides of adjacent microundulations are close together, the absorbent fibers of the bat, because of the pretreated state, having stored mechanical energy in a predetermined selected direction, the pretreated bat as it resides in the tampon, being moisture-sensitive, responsive to small amounts of liquid to cause release of the mechanical energy and to expand in the given direction to cause rapid expansion of the exterior of the tampon.

In preferred embodiments the tampon is comprised of carded or uncarded fibers; the tampon comprises the pretreated bat disposed about an absorptive core of different material.

BRIEF DESCRIPTION OF DRAWINGS

FIGS. 14, 15 and 16 are microphotographs taken of tampon materials, namely bleached blend cotton, super-inflated rayon known as S. I. Rayon, and Rayon Tow, respectively.

DESCRIPTION OF PREFERRED EMBODIMENTS

Figure 1D:
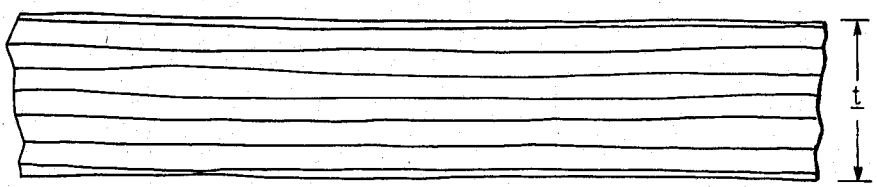
FIG. 1d for comparison is a diagrammatic view of the bat prior to longitudinal compaction in accordance with FIG. 1.
Figure 1:
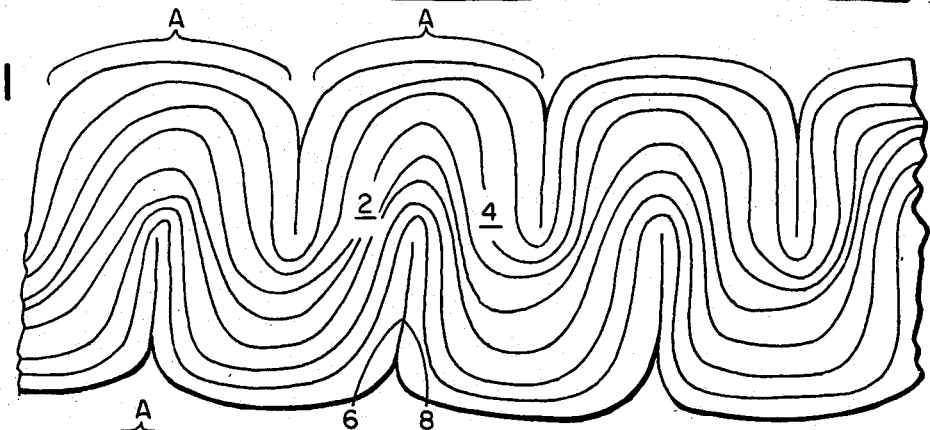
FIG. 1 is a magnified diagrammatic view in longitudinal cross section of bat of unbonded fibers in the flat, having a series of closely adjacent microundulations as a result of longitudinal compressive pretreatment. The bat is shown as it comes from the longitudinal compacting device before being fed to the tampon making mold.

According to the invention the exterior at least of a tampon is formed from a bat of substantially aligned loose, unbonded fibers which, in bat form, prior to tampon making, is subjected to longitudinal compressive pretreatment to provide a bat which has microundulations essentially as shown in the highly magnified diagrammatic cross-sectional view of FIG. 1.

FIG. 1d illustrates the bat of loose fibers before compressive action. Such a bat may be obtained, e.g., by carding cotton fibers or rayon fibers of staple length or employing other bat forming thickness such as air layering or employing tow. The bat may have a thickness t which will vary with the weight of bat being employed. For instance, in the first preferred embodiment to be described, the bat has a weight of 10 grams per linear meter and has an uncompressed thickness t of 0.025 inch. In other embodiments the bat may, for instance, be of 20 grams per linear meter density in the untreated state with a thickness t of 0.050 inch, or 30 grams per linear meter with an untreated thickness t of 0.075 inch.

The microundulated bat of FIG. 1 has a number of undulating ridges 2, 4 characterized by sides 6 and 8 of adjacent ridges 2 and 4 being closely adjacent to one another as a result of the application of longitudinal compressive forces. During the pretreatment the individual fibers of the bat undergo slippage and rearrangement as the result of the longitudinal compressive action, as well as bending through the tortuous cross section as depicted in FIG. 1. The longitudinal compressive action or microcreping, used to produce the microundulations is achieved by compressing the web in its own plane, in the direction of its length (direction of orientation of the fibers) by compressive forces exerted substantially parallel to the longitudinal direction of the material, while the material is confined in a small dimension treatment cavity. Presently preferred for accomplishing this action is the two-roll microcreper invented by Messrs. Richard R. Walton and George E. Munchbach, inventors herein, U.S. Pat. No. 4,142,278, which is hereby incorporated by reference.

It is realized that the longitudinally compacted bat as shown in FIG. 1, if compacted to the appropriate degree, will retain its longitudinally compressed, microundulated condition so long as it is kept dry. This web may be so pretreated beforehand and rolled up and stored in a roll, or it may be produced in line with the tampon-making machine.

Figure 1A:
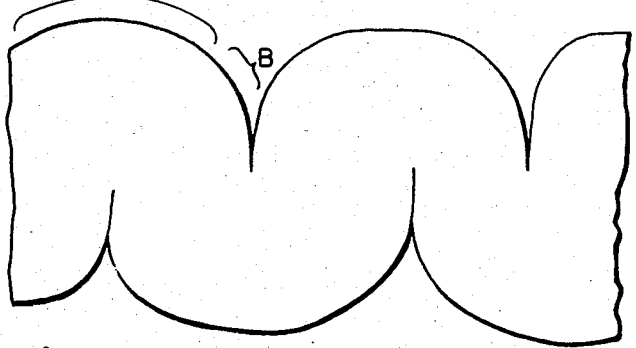
FIG. 1a is a cross sectional view similar to FIG. 1, showing the initial dynamic response of the microundulations of the longitudinally compressed bat when the treated bat is exposed to a small quantity of liquid in vitro.
Figure 1E:
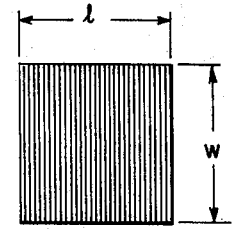
FIG. 1e is a diagrammatic plan view of a square area of longitudinally compressed bat prior to exposure to liquid with the density of microundulations suggested by a concentration of parallel lines.
Figure 1B:
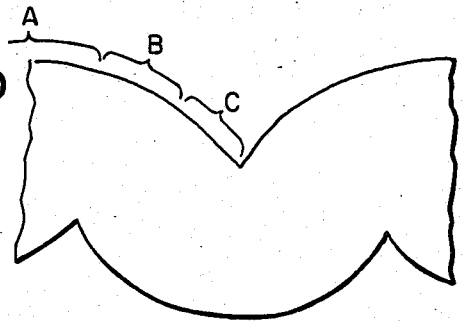
FIG. 1b is a view similar to FIG. 1a showing a further stage in the progressive expansive movement of the microundulations and progressive exposure of fresh absorptive area as expansion occurs.
Figure 1F:
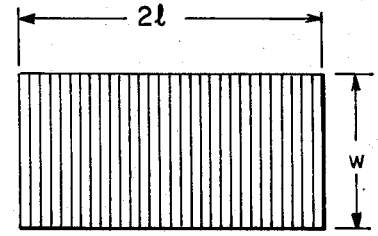
FIG. 1f is a view similar to FIG. 1e, illustrating the square area of bat of FIG. 1e after exposure to liquid, representing the extent of expansion of the bat in the lengthwise direction, by the increased spacing of the parallel lines, no expansion in the widthwise direction having occurred.
Figure 12:
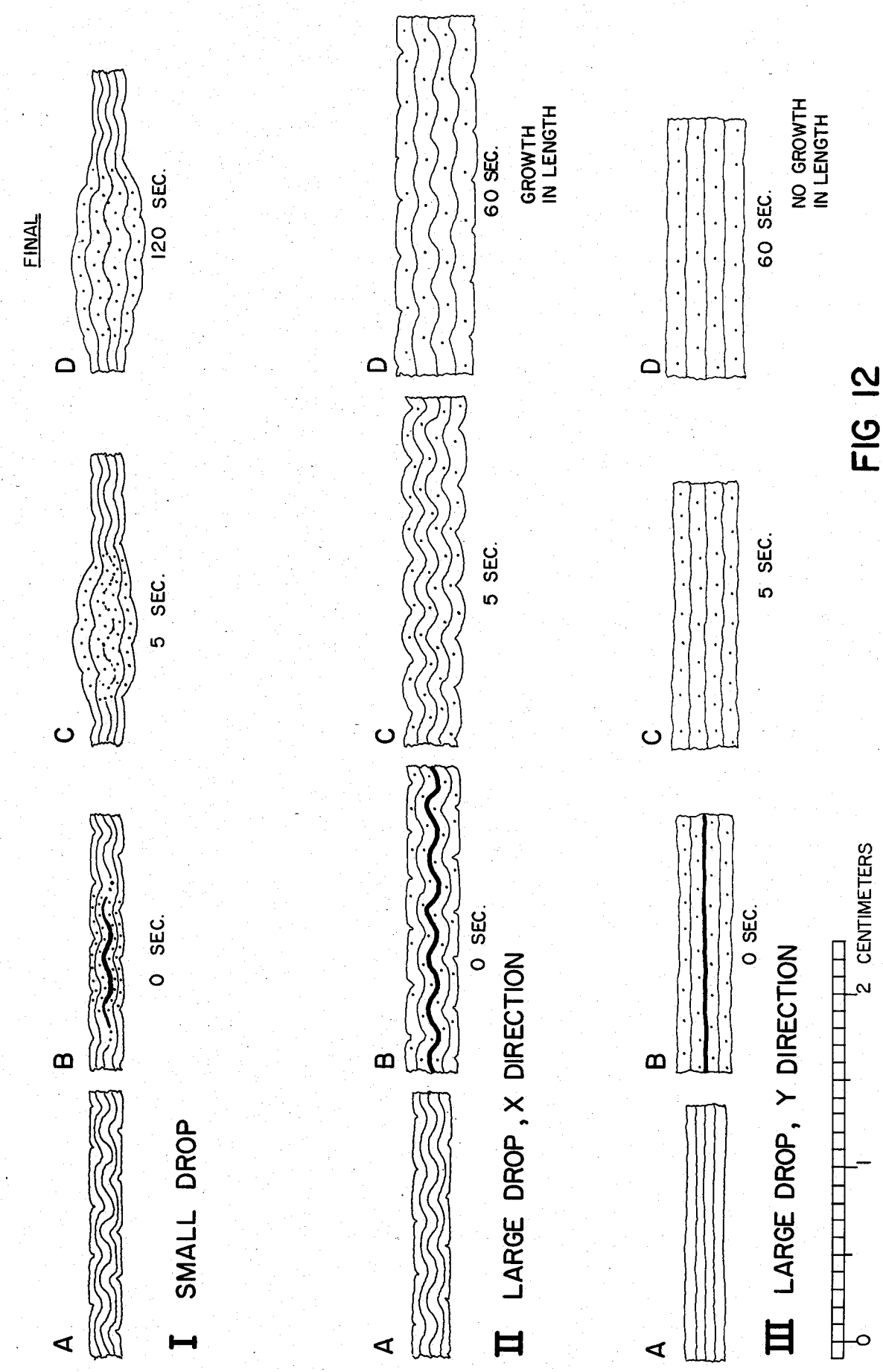
FIG. 12 is a graphic illustration of photographs of microundulated specimens taken during and after administration of dyed drops of water.

FIGS. 1a, b and c and the graphic representation of photographs of an actual experimental demonstration, FIG. 12, (described in detail further below) illustrate the reaction of such a microundulated bat in vitro to exposure to liquid, as an indication of the behavior of this web when incorporated in a tampon. FIG. 1a and Series I of FIG. 12 show the effect upon the microundulated bat of exposure of the bat to only a small amount of liquid. The microundulated structure swiftly responds in two ways. As demonstrated in FIG. 12, stage C of Series I, (5 seconds after application of the liquid) the immediately adjacent fibers rapidly conduct liquid to adjoining fibers so that there is an immediate and uniform liquid distribution throughout a large area of the treated bat, much more so than if the bat were untreated, due to the closeness and unique interengagement of the rearranged fibers as the result of their microundulated condition. Secondly, as demonstrated by comparison of Series II with Series III of FIG. 12, the contacting liquid initiates the release of the substantial stored, directional mechanical energy that has been set into the mass by the microcreping process. It will be seen that the web expands in one predefined direction as the small microundulations or ridges begin to relax and move. The individual fibers in exposed region, A, move in a dynamic way, adjusting the relationship between individual fibers and providing, though slight, a disturbance to the fluid that seeks to enter. This is of particular importance because the menstrual fluid includes cells, blood and secretions that tend to mat and coagulate and to some extent block the flow of liquid into the absorbing structure. The dynamic fiber action aids in the movement of this fluid into the interior. Furthermore, by comparison of FIGS. 1 and 1a, it is seen that during the absorptive process, additional fresh absorptive area, B, has been exposed. This action continues as illustrated in FIG. 1b in which, after application of still more fluid, still further fresh absorptive area, C, is exposed. This uncovering of fresh fiber surface reduces the blocking effect of secretions by presenting a greater surface area for liquid transfer.

Figure 1C:
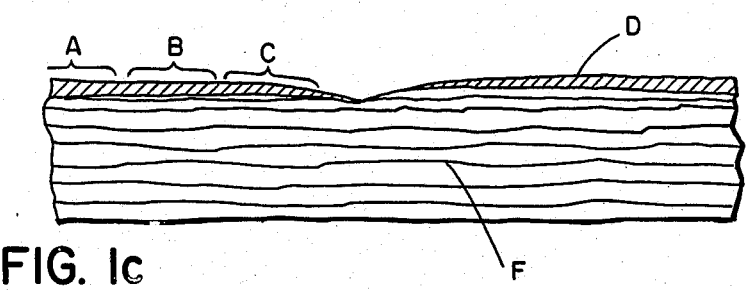
FIG. 1c is a view similar to FIGS. 1a and 1b, showing the bat when expansion of the microundulations is complete.

In FIG. 1c is shown the ultimate full extension of the microundulated bat almost to its full original length, as a result of the ultimate release of the stored unidirectional mechanical energy. (To similar effect is stage D in Series II of FIG. 12.)

For illustrative purposes in FIG. 1c, varying thicknesses of accumulated material D are shown in the areas corresponding to areas A, B and C to symbolize the variation in matting that may occur in actual use due to the progressive exposure of fresh surface. Also, a certain kinkiness is shown remaining in the individual fibers, F, in FIG. 1c as a result of the longitudinal compressive treatment in gross of the bat of fibers. This contributes interstitial volume to the mass that can add to the absorptive effects of the tampon.

Various bat materials respond somewhat differently to the longitudinal compressive treatment process, so that while preserving the ability of substantial dimensional recovery, different amounts of longitudinal compaction are appropriate. A preferred material is a bat of staple rayon with the fibers aligned essentially in the longitudinal direction of the bat, (though the fibers may be somewhat mechanically interengaged, e.g. if carded). It is presently preferred to compact this bat 50%, that is, to shorten the bat by one half and increase its density twofold by the microcreping process. In the case of bleached cotton, which has a somewhat more resilient nature, and as well a greater portion of fibers which are not entirely aligned with the longitudinal direction of the bat, the degree of preferred compaction is less, e.g. in the 25 to 30% range.

In general, it is found that a useful degree of the longitudinal precompaction in bat form can be applied to most common tampon-forming fibers, the range of useful preshortening being between about 20% to 60% of the original length of the fibers in the case of carded fibers.

The number of microundulations to be formed to take advantage of the invention will vary with the nature and thickness of the material circumstances, but in all cases the bat must have microundulations, i.e. there must be at least 10 or more undulations per inch, and these must be compacted together, with sides of the microundulations being closely adjacent to one another, in order to generate a useful force of expansion as described herein. In the preferred case of using a thin, 10 gram per linear meter untreated density bat for forming the exterior of a tampon about an insert, preferably as many as 40 microundulations per inch are employed and the preferred minimum number of microundulations is about 25. For a 20 gram per linear meter bat, the most preferred number is about 30 and the preferred minimum is about 20 microundulations per inch. In the case of a bat of 30 grams per linear meter untreated density (which might be the only absorptive constituent of the tampon) the most preferred number is 25 microundulations per inch and the preferred minimum is about 15 microundulations per inch. These numbers refer to the number of ridges to be produced prior to introduction into the tampon mold. Further compaction in the tampon mold increases the density of the ridges of microcreping substantially.

Figure 3:
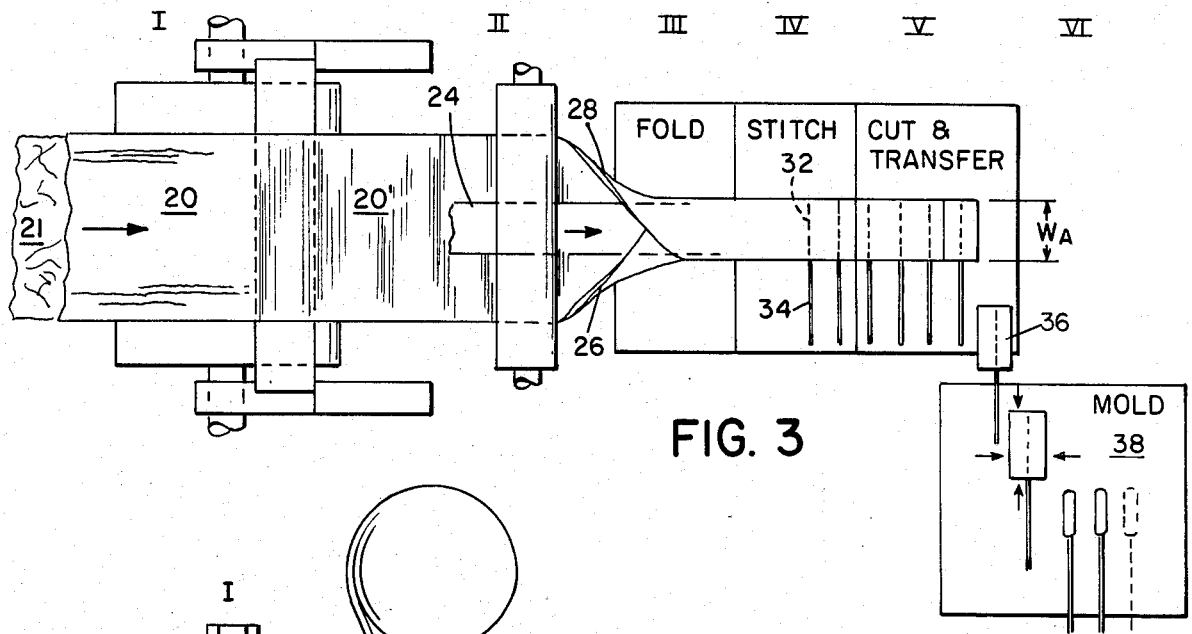
FIG. 3 is a plan view of the apparatus of FIG. 2.
Figure 2:
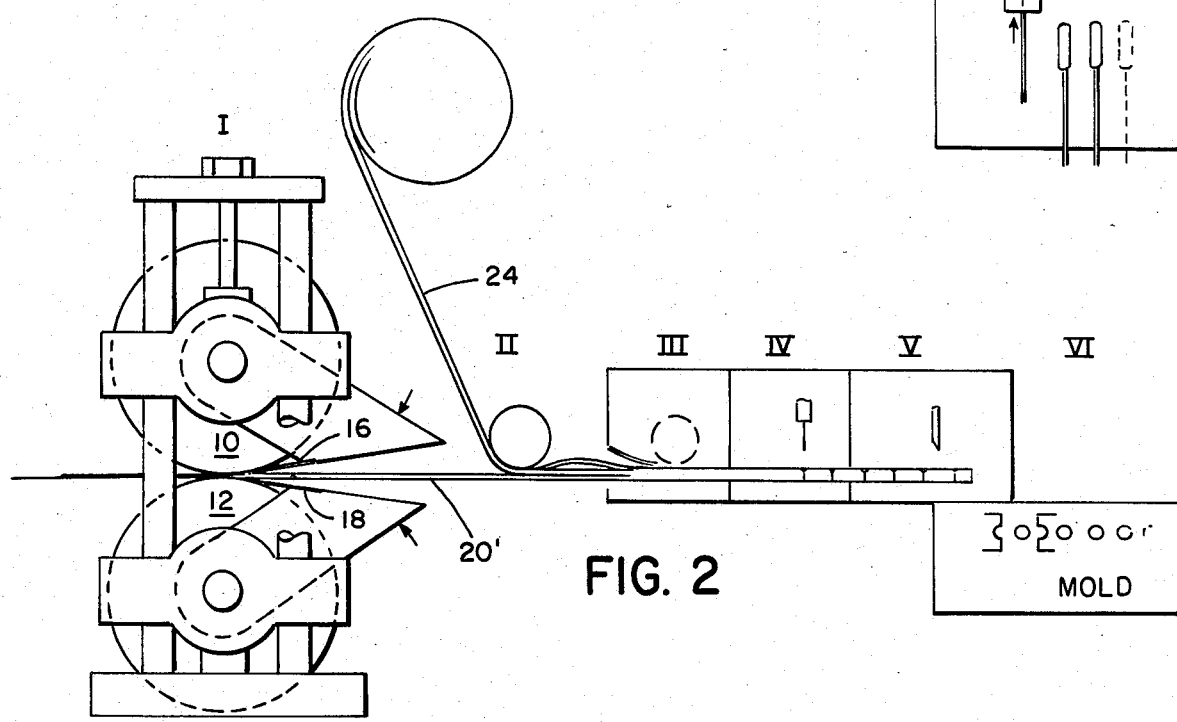
FIG. 2 is a plan view of apparatus for pretreating the bat and subsequently forming a tampon according to one preferred embodiment of the invention.
Figure 4:
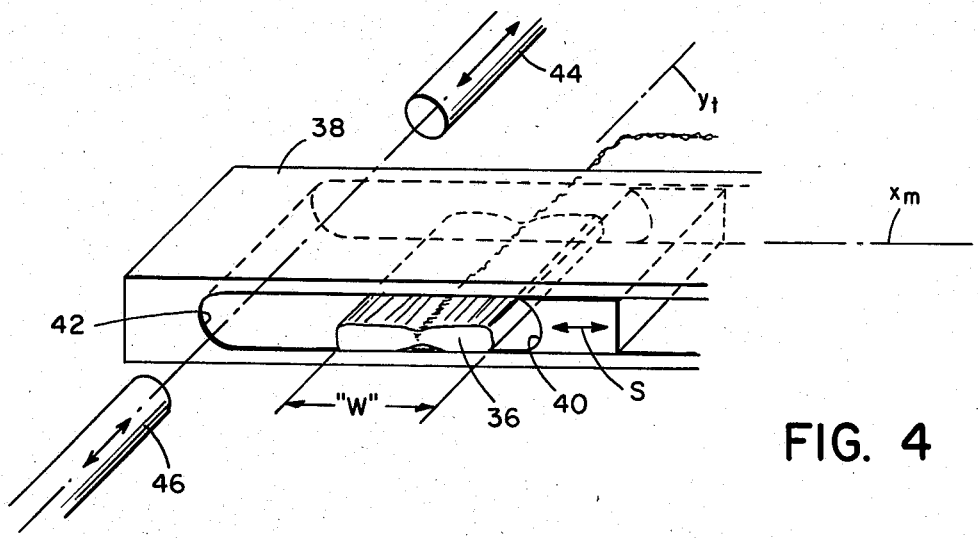
FIGS. 4, 4a and 4b are large-scale diagrammatic views of the tampon-making mold of FIGS. 2 and 3 in the progressive act of forming a tampon.
Figure 4A:
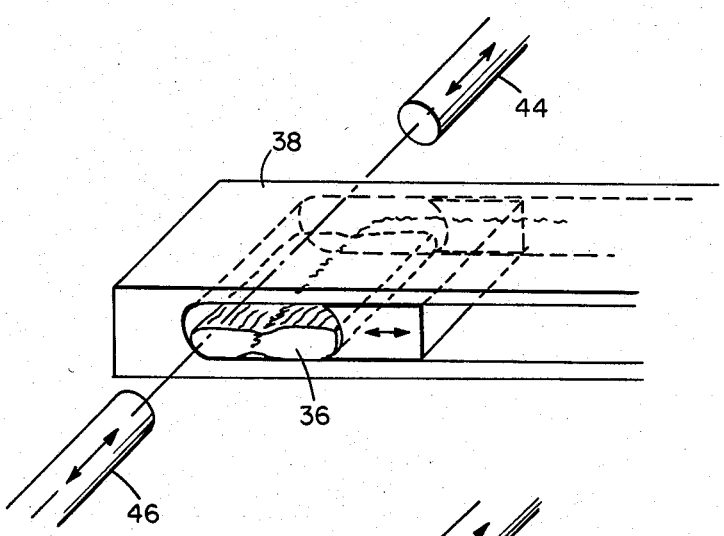

FIGS. 2-4 illustrate the manufacture of a preferred tampon. At station, I, a two-roll microcreper receives an untreated bat 20 of carded tampon-forming fibers, which are essentially unbonded to each other and generally aligned with the machine direction. This bat 20 lies upon a nonwoven hydrophyllic tampon outer layer 21, typically a bonded cellulosic fabric of about 0.003 inch thickness as used in the trade. As more fully described in U.S. Pat. No. 4,142,278, the microcreper employs a drive nip for driving the bat along a path formed by stable surfaces of a pair of oppositely rotating drive rolls, 10 and 12 in FIGS. 2 and 2a. A retarding device on the exit side of the nip is formed by at least one and preferably two relatively stationary retarding members 16 and 18.

Figure 2A:
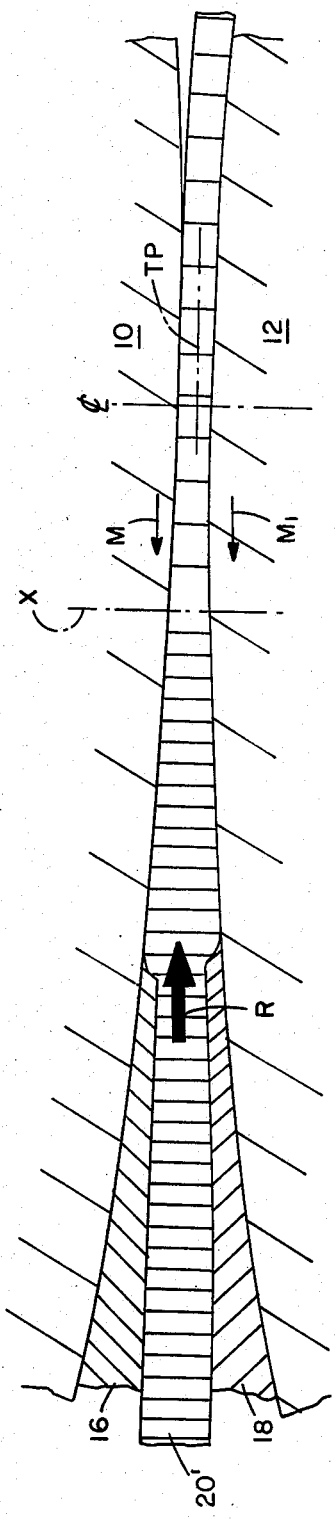
FIG. 2a is a diagrammatic side view in enlarged scale of the longitudinal compressive action of the 2-roll microcreper upon the bat of fibers.

The initial parts of these retarding members define a means for providing damming forces that act essentially in the longitudinal direction of the bat, i.e. in FIG. 2a in the direction of arrow, R. The assemblage of the fresh bat of fibers 20 and the thin outer layer 21 is driven by the rotating rolls 10 and 12 past the center line, C-L, FIG. 2a, and is propelled forward by the forces, M and M-1, applied by the two rotating rolls. At position, X, the material begins to slip on the rolls and compresses longitudinally in the treatment cavity formed by the continuing surfaces of the rolls. This compression is suggested by the blocks of narrower width in FIG. 2a. The resistance that leads to this compression is provided by the two retarding members 16 and 18. In the case of the bat of fibers of the present invention, the fibers in the region between line, X, and the ends of the retarding members are formed into microundulations in the form shown in FIG. 1 in which adjacent ridges of the microundulated structure tightly abut one another in the treatment cavity as a result of the longitudinal compressive forces applied. In general, as mentioned above, there will be at least 10 microundulations per inch for even the thickest material that might be employed in a tampon and typically more depending upon the thickness of the bat being treated and the nature of the material selected.

From this treatment the web is led either to a temporary storage roll or to the further tampon-making equipment with care being observed to avoid substantial tension to avoid stretching thus to preserve the close adjacency of the ridges of the microundulations.

In the preferred embodiment, as mentioned before, the bat 20 of fibers is comprised of carded rayon staple fibers, 10 grams per meter and it, together with the thin outer layer 21, is compressed 50% by the microcreper, i.e. it is shortened by half and its weight after treatment is 20 grams per meter. At station II in the machine of FIG. 2 an unmicrocreped insert layer 24 of hydrophyllic material, preferably an insert of carded bleached blend or of highly absorbent carded staple rayon fibers, having a weight of 40 grams per meter, is introduced. This insert layer is only about one third as wide as the microcreped layer 20. In the most preferred embodiment this material is so called S. I. Rayon, staple fiber obtainable from Courtaulds, Ltd., of Manchester, England. This insert layer 24 is applied to the middle of the pretreated bat 20' as depicted in FIG. 2. At station III, as shown, edge 26 of the microundulated sheet is folded over the insert and then opposite edge 28 is folded over the insert to provide a folded assembly. At stage IV, the tampon-end of the withdrawal string is secured across the width of the assembly by stitching 32. A free length 34 of the string extends beyond the assembly. At stage, V, a tampon blank of 1¾ inch length in the axial direction of the bat is cut from this continuous assembly, the width $W_A$ of the bat and insert assembly being in the folded condition about 4 inches. This tampon blank 36 is moved sideways relative to the machine direction into the tampon mold 38.

Figures 5, 6, 6A, 6B:
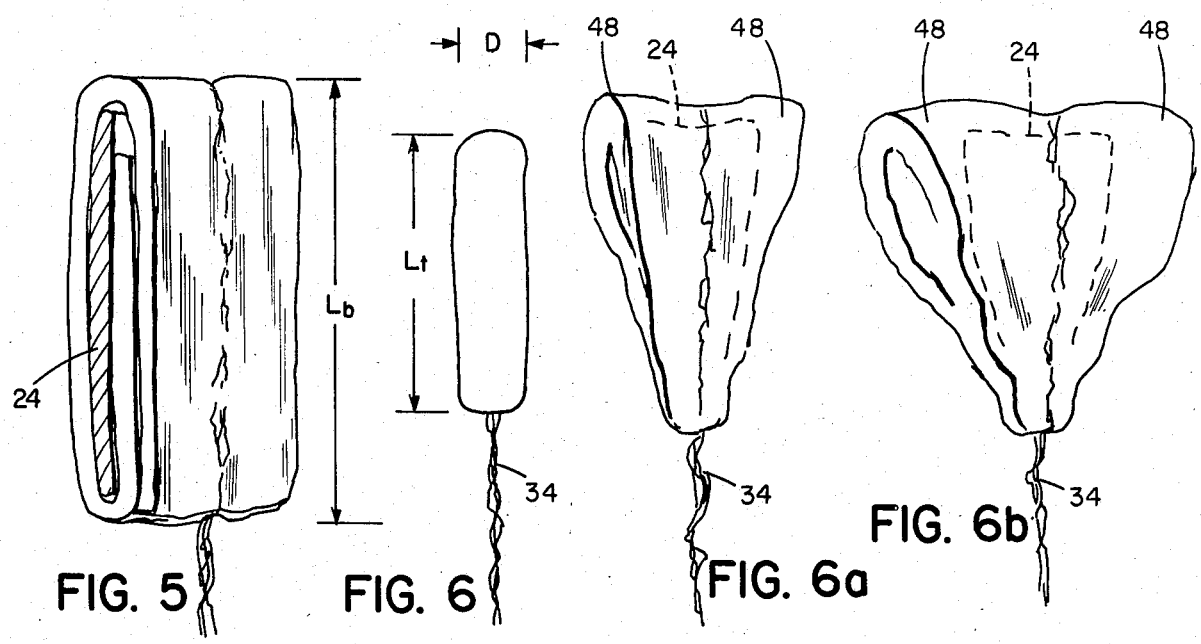
FIG. 5 is a perspective view of the tampon blank prior to insertion into the mold of FIG. 4.
FIG. 6 depicts a finished tampon after it has been subjected to the tampon-making steps of FIGS. 4a and 4b.
FIG. 6a illustrates the tampon of FIG. 6 after having its head end exposed in vitro to a small amount of liquid.
FIG. 6b depicts the full in vitro expansion of the head end of the tampon after exposure to more liquid.
Figure 4B:
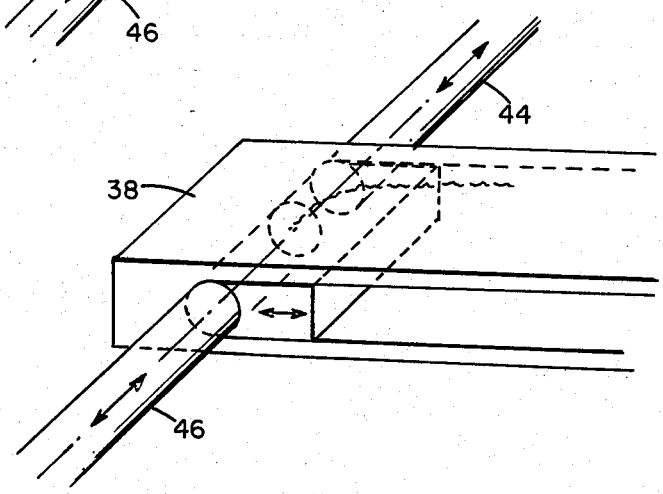

Referring to the diagrams of FIGS. 4–4b, the tampon blank 36 is advanced sideways in direction by a concave mold surface 40 until the blank 36 reaches an opposing concave mold surface 42 which forces the blank into a cylindrical configuration. The microcreped ridges are denoted in FIG. 4 by parallel lines that extend transversely to the axis $X_M$ of the foregoing microcreping machine, or parallel to axis $Y_t$, the axis of the tampon mold. The effect of this compression is to reduce the size and increase the density of the microundulations formed by the previous microcreping action. After the sideways compression, forming the blank 36 into the confines of a cylinder, axial compression rams 44 and 46, aligned with the cylinder, parallel to axis $Y_T$, act to compress the tampon blank lengthwise to produce the tampon in final form, as depicted in FIG. 6, with typical dimensions (depending to some extent on the absorbent grade of tampon desired) length $L_t$ of 1¾ inch and diameter D equal to ½ inch. For side-by-side comparison in FIG. 5, the blank (4" long, 1¾" wide) from which the tampon was formed is depicted, with the lines of the microundulations denoted in both instances.

In the perspective view of the tampon blank, FIG. 5, it is seen that the edge of the insert material 24 lies at the same cutting plane as the cut edge of the outer microundulated bat and cover assemblage.

A unique function of the invention is that this insert, though present at this cutting plane because in this embodiment of the method of manufacture, can be immediately enveloped by the microundulated material as soon as moisture contacts the finished tampon. When the tampon of FIG. 6 has its head exposed to even a slight amount of liquid, the liquid is seen to almost race through the substance of the microundulated bat, and the bat expands significantly in almost a flowering mode, as depicted in FIG. 6a. Thus, the insert 24, the position of which is suggested by the dotted lines in FIGS. 6a, becomes protected by the outlying wings 48 of the expanding bat. This enveloping action can be important if the insert has such strong absorbing capability or other feature that makes it undesirable that it contact the mucosal surfaces of the vagina. As seen in vivo, the expansion of the outer bat continues, as liquid contacts the tampon. It is believed that in vivo the tampon surface behaves in a way suggested by that which is observed in vitro, see FIGS. 1–1e. Thus, the microundulated surface of the tampon remains active even after receiving the final compressional forces of the final tampon-molding procedure. The expansion of the microundulated surface in controlled direction uniformly exposes fresh area, and distributes the liquid effectively through its mass, and thence by intimate contact, into the absorptive insert 24. The expanded shape of the tampon as shown, by normal movements of the wearer, is believed to align in an effective way, for optimum position to intercept fluid discharge very efficiently. The overall effect of this tampon is to prevent early leakage and, in a simple-to-construct form, enables extremely efficient utilization of the absorptive capacity of the materials present.

The maximum degree of compaction to be employed depends, e.g. upon the nature of the fibers, the form in which the fibers are treated and the temperature of treatment, as well as upon the conditions of actual molding of the final tampon. In the case of carded fibers the preferable range generally is 20% to 60%. Experiments have suggested that other materials, e.g. tow may be compressed as much as 85%. The maximum amount for any particular situation can be determined on the basis of simple trials, observing the degree to which the treated material (microundulated) can recover its length in response to contact with liquid.

While in the foregoing embodiment a core or insert of uncompressed material has been employed, it should be understood that a number of advantages, for instance, greater power of expansion and greater fiber movement, can be obtained by also pretreating the core to a longitudinal compressive treatment as described above. Indeed, tampons made entirely of a single thick bat of fibers pretreated by longitudinal compression are possible. In this case, due to the thickness, the individual ridges are larger, producing fewer per lineal measure, for instance, this approach may be effective down to about 10 closely adjacent undulations per inch.

It will be understood that if the wave length of the undulations, that is the length of material constituting each ridge, is too long, there is a sudden loss of directional mechanical power available because of inability of a long straight column of material to transmit effectively the expansional force (much as a column which is too long suffers buckling instead of resisting a compressional force which is placed upon it). This has particular application to the radial expansive forces which are employed according to the invention for preventing early leakage and explains the importance that the undulations be microundulations for the purpose of this invention.

Figure 7:
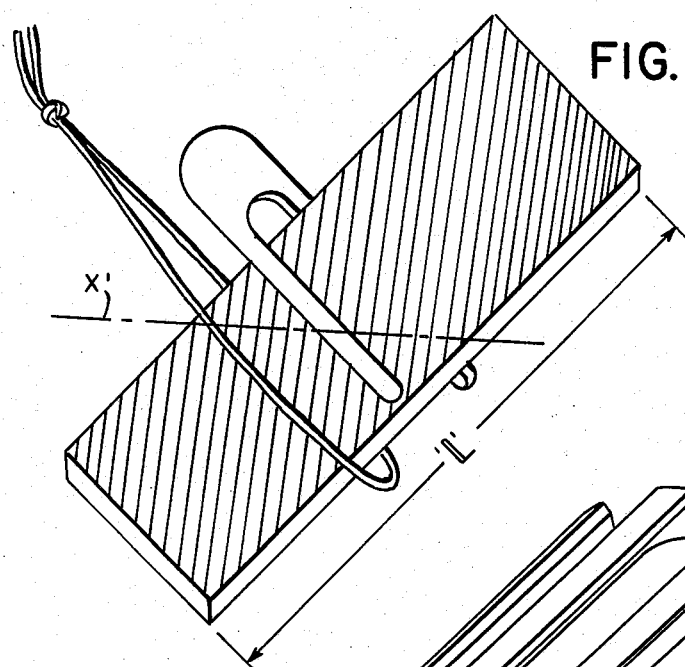
FIG. 7, for another embodiment, depicts a microundulated tampon blank for use in making a tampon by a rolling method.
Figure 8:
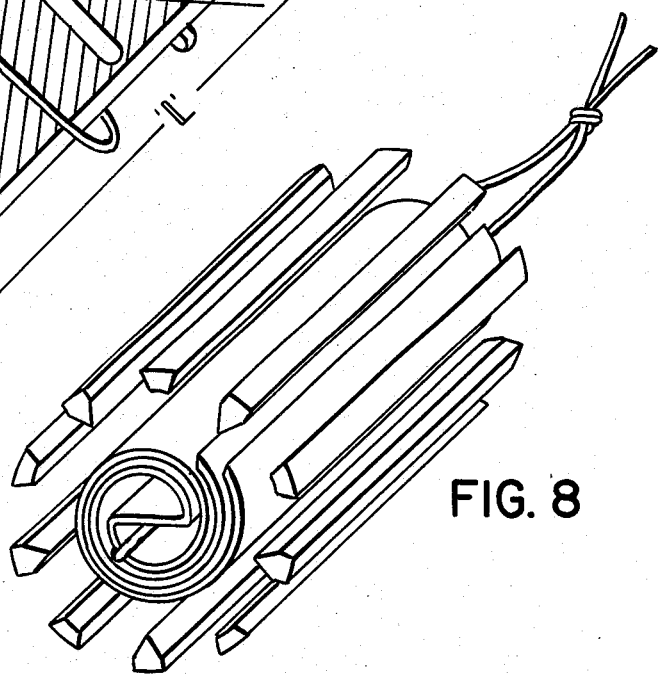
FIG. 8 shows the rolled tampon blank inserted in the tampon-making die and FIG. 9 shows the finished tampon in accordance with this embodiment.
Figure 9:
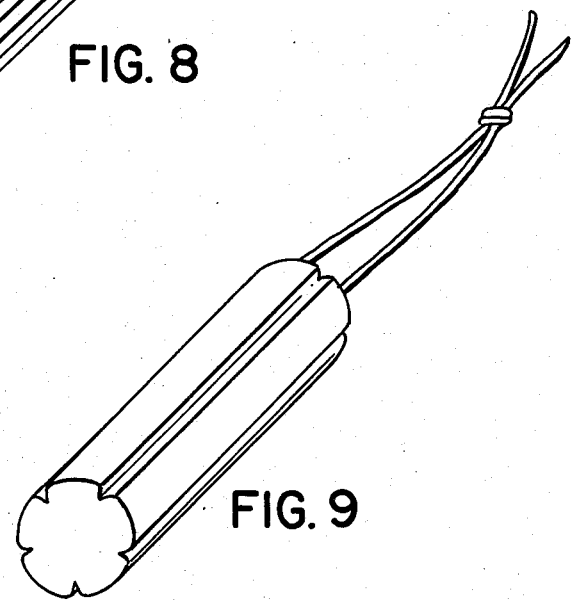

In FIG. 7 is shown a tampon blank comprising an elongated strip of fiber bat, and, as suggested by the diagonal lines, the pretreatment under longitudinal compaction has occurred on the diagonal axis $X^1$. This may be accomplished by cutting the specimen on the bias from normal transversely microundulated bat as produced by the machine shown in FIGS. 2 and 2a, or this or a one blade microcreping machine may be adapted by use of helically shaped blades and associated surfaces to effect its compressive action at an acute angle to the direction of feed through the machine. The tampon blank in FIG. 7 is initially rolled into a cylinder as shown in FIG. 8 and inserted within a radially acting die which compresses the roll to the final tampon form as shown in FIG. 9. The slanted lines on the surface of FIG. 9 suggest the diagonal direction of the microcreped ridges of the microundulations that exist in the resultant tampon.

When exposed to liquid the diagonal nature of the compacted ridges produces an expansion at right angles to the lines of compression. This effects a component of longitudinal as well as radial growth in the tampon as part of the expansion. In tampons previously formed using the general procedure illustrated in FIG. 8, there has been difficulty because, when exposed to menstrual fluid, the tampons at times become too large in diameter and are uncomfortable to remove. The process as described herein enables some of the growth to be expressed axially, thus reducing the total radial growth of the mass. This improves the removability of the tampon. Furthermore, by precompressive longitudinal treatment of the web, the roll size required to be introduced into the die of FIG. 8 is of reduced dimension and enables use of a much more convenient machine and operation in forming the tampon, because the smaller roll is easier to handle.

Figure 10:
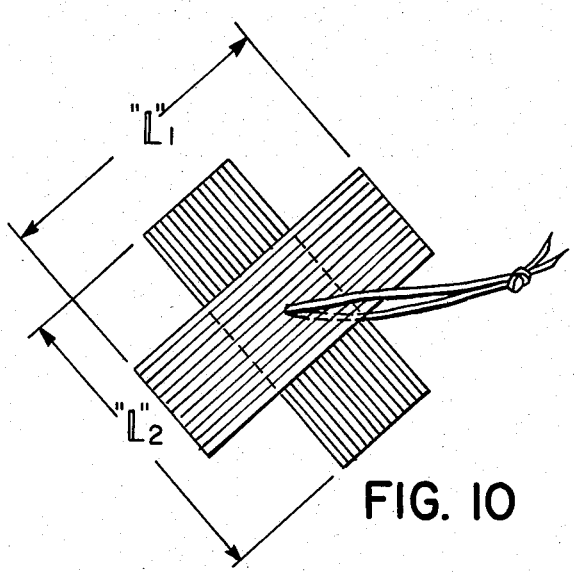
FIGS. 10, 10a and 10b show still other alternate methods of forming a blank for a tampon.
Figure 11:
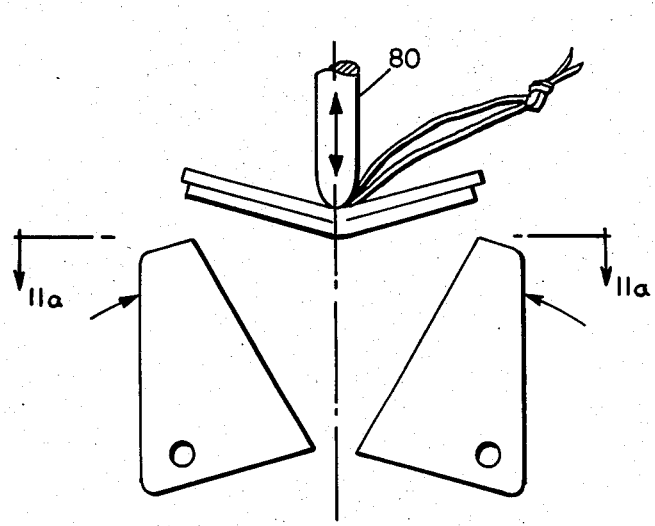
FIG. 11 depicts the various molding stages and FIG. 11a depicts the final formation of the tampon.
Figure 11A:
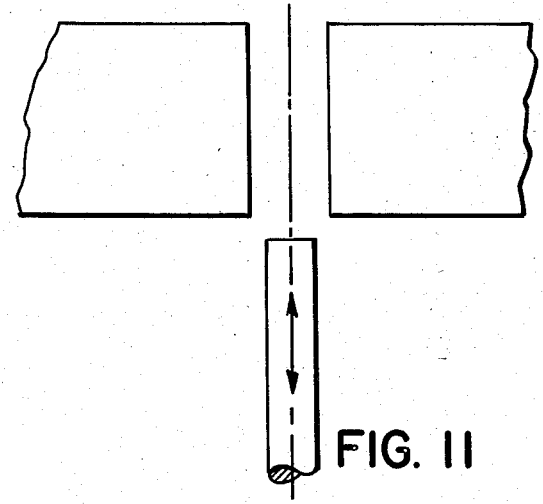

In the embodiment of FIG. 10, two elongated segments of bat material that in crossed configuration form a tampon blank have the ridges of the pretreatment of longitudinal compression aligned with the long dimension of the segments. Thus, when these segments are bent upwards to parallel the axis of the tampon by action of the plunger 80 (FIG. 11), these lines of compression will be parallel to the axis of the tampon and will enable radial growth of the tampon upon exposure of liquid in manner similar to that of the first embodiment.

Figure 10A:
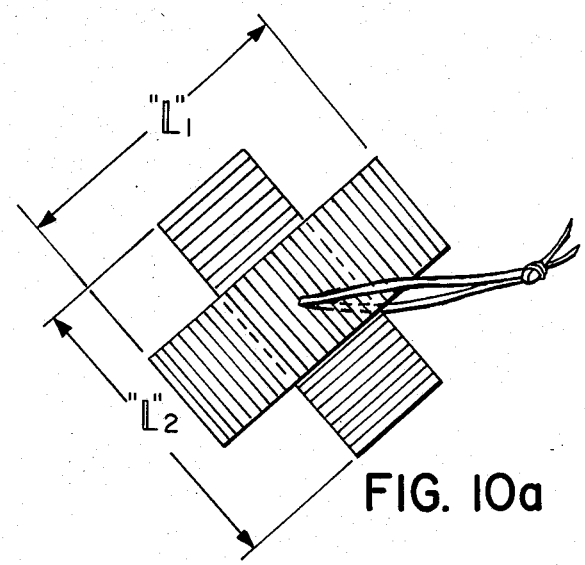
Figure 10B:
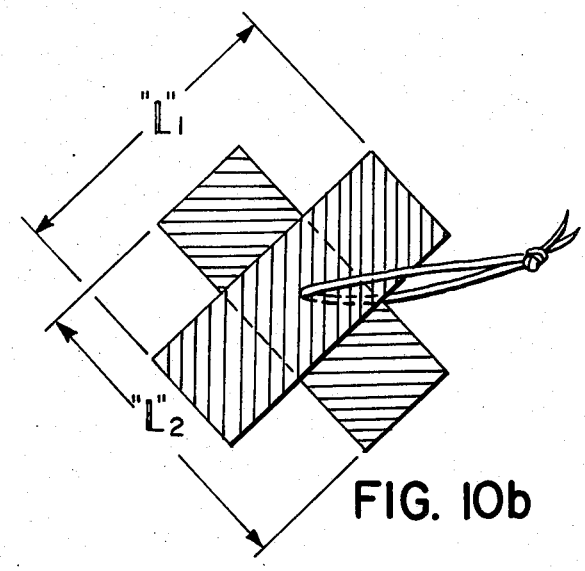

Other embodiments are shown in FIGS. 10a and 10b. In FIG. 10a, the ridges of the pretreatment of longitudinal compression are at 90° to the long dimension of the segments. When the segments are bent upwards to parallel the axis of the tampon these lines will be transverse to the axis and will enable longitudinal expansion of the tampon upon exposure to liquid. In FIG. 10b, the ridges are at 45° to the long dimension of the tampon, and are also at 45° to the tampon axis when the segments are bent upwards. This configuration will enable both radial and longitudinal expansion upon exposure of liquid in manner similar to the above embodiments. This dynamic movement of the fibers during absorption, as a result of relaxation of the mechanical, directional energy is also a reliable attribute of these embodiments.

OTHER CONSTRUCTIONS

Numerous other constructions can take advantage of the invention in other ways. Thus, if a tampon blank is made by cutting a rearranged stack of webs, the cut edges of all layers in the final tampon may be exposed to the vaginal walls. Such contact of some materials may be detrimental. This contact can be substantially prevented by the shielding effect provided by a microundulated cover layer. Though cut to the same dimension in the blank, when it is contacted with liquid it will immediately expand over and shield the layer that requires shielding.

Improved Tampon Molding

A further advantage of the invention will be apparent from consideration of the action that occurs in tampons that are formed with a degree of compression in the direction of the axis of the tampon. This mold action is desirable in that it stabilizes the compressed final form of the tampon and enables some lengthwise growth of the tampon, which is observed to make the tampon susceptible of elongation during withdrawal, thus to tend to decrease the circumference of the tampon, making the withdrawal action less uncomfortable to the wearer.

The problem observed with this axial compression in the tampon mold is similar to what is known as the "rope and tube" effect. The tampon, before it receives the axial force, is confined in a cylinder, just as one might confine a segment of rope in a tube of similar diameter. As is well known, if one seeks to advance the rope by pushing on the end of it, a phenomenon occurs that makes it difficult for the pushing forces to advance the rope. As the pressure is applied on the end of the rope, there is a tendency for the rope, as it is compressed, to swell. As this swelling occurs, the exterior surface of the rope near its end bears with greater pressure against the cylindrical wall of the tube. This introduces frictional drag. And, therefore, as the pressure on the end of the rope increases and as the swelling of the ends occurs, greater and greater frictional drag occurs, and a very great force is required, or indeed the rope cannot be moved. This same phenomenon impedes the compression of the interior midsection of a tampon. The result is that the tampon is not uniformly compacted and hence does not have uniform absorptive qualities. Indeed, there are occasions when the ends of the tampon will be so compressed as to be very hard, and will neither readily accept fluid nor readily expand, to the detriment of the performance of the tampon.

In the case of forming the tampon blank from pre-longitudinally compacted bat as herein disclosed, a significant amount of the total compaction that is desired has already taken place. Therefore, for compressing the ends of the tampon, less radial swelling will occur in the mold, and furthermore, less compressive force needs to be delivered ultimately to the center of the tampon because of significant amount of precompaction that has already taken place as a prior step to molding. The overall effect, therefore, of using the pretreated material according to the invention, is to reduce the hard end problem and to achieve a tampon of greater uniformity of compaction, and therefore of greater uniformity in absorption.

Types of Bat

While carded bats of cotton or rayon fibers can readily be employed according to the invention, the invention is not so limited. For instance, a bat or array of monofilaments, e.g. so-called "tow", can be treated as a bat by being passed through the microcreper to produce microundulations in an ordered manner to the assembly. This can avoid the step of carding, and as well, in some cases, can avoid the need to crimp the fibers in the fiber-making process, e.g. wavy gear crimp or forcing the fibers through a stuffing box, from which the crimped fiber is then pulled and stretched.

Experimental Demonstration of Properties of Efficient Liquid Transfer and Expansion in Preferential Direction (FIG. 12)

Figure 13:
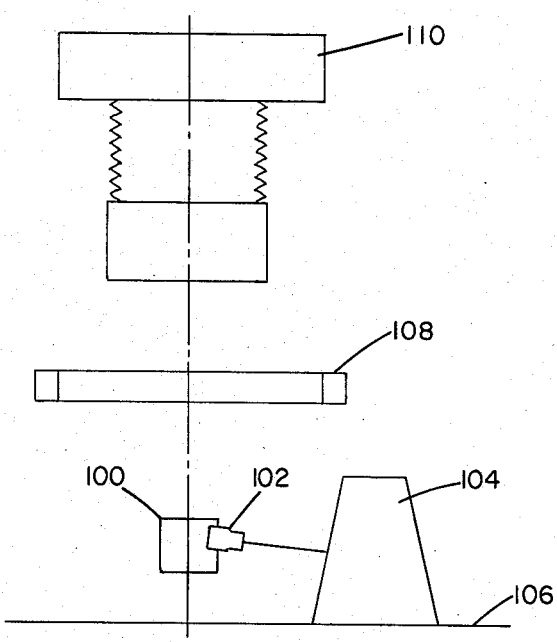
FIG. 13 is a diagram of the camera setup employed to take the photographs upon which the drawings of FIG. 12 are based.

The effects of liquid are illustrated on sample segments of a bat of normal tampon material (bleached blend cotton) which has been treated to have the microundulations that have been described. This bat, composed of a number of superposed carded layers, was processed as a unit through the two roll microcreper, referred to above, to achieve the microundulated condition. The drawings of FIG. 12 are representative of actual photographs taken according to the following procedure, using the apparatus as shown in FIG. 13. The specimen, approximately one-half inch long, was gripped by a spring card holder 102 and held vertically as shown by means of a cork base 104 resting on surface 106. The upper edge of the specimen 100 was illuminated by ring lamp 108. A camera 110 was disposed above the specimen 100, as shown. In each series of tests water containing dye (fast green FCF histological dye, National Aniline Division, Cenco Central Scientific Co.) was employed.

In series I of the tests, at stage A the machine direction edge of the specimen is shown prior to introduction of liquid. The microundulated structure is visible and the make-up of the web by a number of carded layers is suggested. A one microlitre drop was then applied to the specimen and simultaneously the photograph of stage B was taken. It is seen that the small drop, immediately upon application, is mostly concentrated in central carded layers of the microundulated sheet, corresponding to the point of application, but as suggested by the stippled area bounding the dark area, some liquid has entered adjacent layers. As seen at stage C, within only 5 seconds of application, very uniform spreading of the liquid has occurred, close to the final degree of stage D taken at 120 seconds after application of the liquid.

Series II and III of FIG. 12 show respectively the effect of a larger drop of the dyed liquid on identical specimens, except that series II views the profile of the specimen in the machine direction, the same as FIG. 1, in which the microundulations are seen, direction X, while series III shows the specimen in the cross-direction, Y, taken along the length of one of the microundulations of the specimen. The large drop was formed by the dipping of a glass rod into the liquid and allowing the first drop to enter the specimen. Stage A is the specimen prior to administration of the drop, stage B represents the specimen immediately upon application of the drop, stage C represents the state of the specimen five seconds after the application of the drop, and stage D represents the state of the specimen 60 seconds after application of the drop. Both specimens were approximately 8 mm square prior to application of the liquid. As suggested by the drawing, the specimen of series II grew in the X direction to the stage D size of 10.4 mm, largely obtained within the first 5 seconds of application of the liquid, whereas as shown in series III, no growth in the Y dimension was observed. In both cases the web was seen to grow significantly in thickness, as illustrated.

Figure 15:
Figure 15:
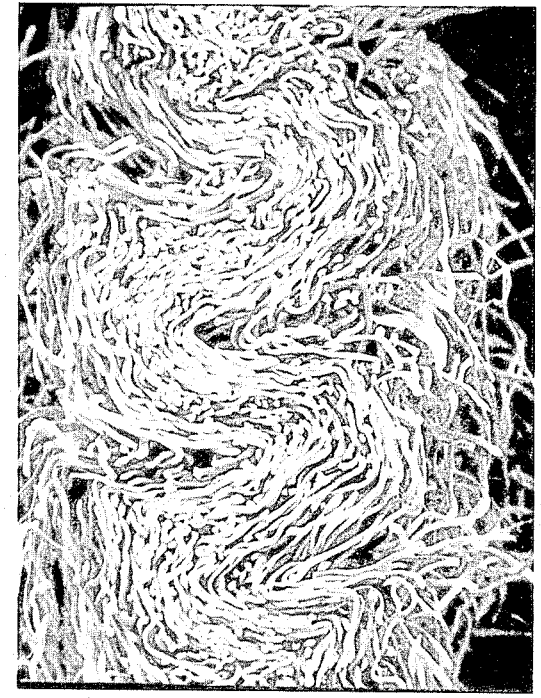
Figure 16:
Figure 16:
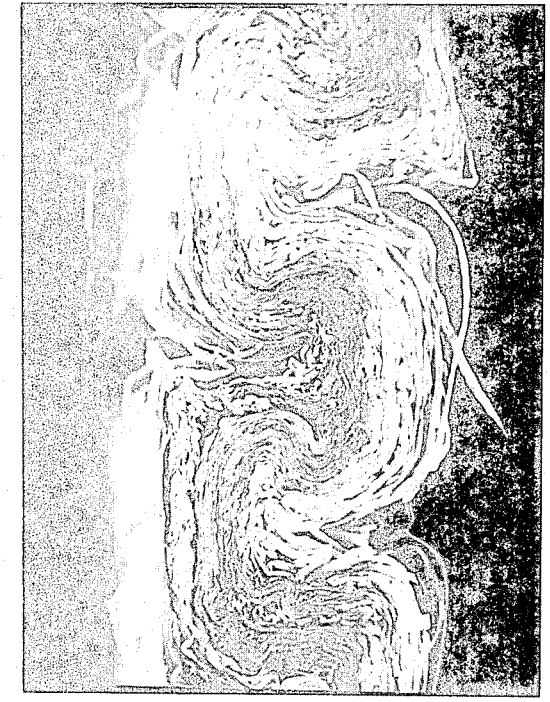

Electron Microscope Photographs of Tampon Materials (FIGS. 14–16)

The photographs shown in FIGS. 14 through 16 were taken at the magnifications indicated, employing a scanning electron microscope (J.O.E.L.-J.S.M.15). Each specimen was cut from a sheet and sputter-coated with gold palladium alloy under approximately 160 microns vacuum using a sputter coater. The coating thickness of about 300–400 angstroms was achieved by a number of successive coatings. The FIG. 14 photographs are of bleached blend cotton, all taken at 30 times magnification, of the edge of respective specimens. The photograph of the uncompacted material shows the fibers mainly aligned in the vertical direction, i.e. the machine direction, with no regularity to the bends that occur in the individual fibers. The other two photographs, of coarse and fine microundulated materials, show a regularity to the configuration of the fibers in the microundulated form described above.

FIGS. 15 and 16 similarly show the microundulated change in the fibers in the respective materials, S.I. Rayon and Rayon Tow.

Figure 17:
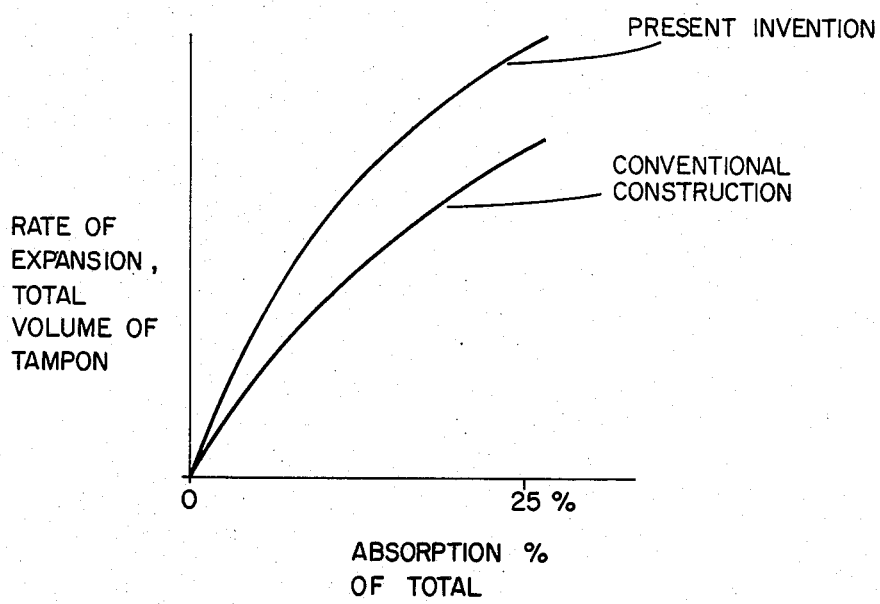
FIG. 17 is a diagrammatic graph showing relative expansion rate of a tampon according to the present invention compared with a tampon of conventional construction.

Improved Initial Expansion Rate (FIG. 17)

One of the most important desired properties of a tampon is that it not permit early leakage. If a tampon allows early leakage, it is discarded by the wearer immediately and judged to be a failure. It is believed by the inventors that there is a close correlation between the expansion capability of a tampon in its early stages of absorption and the tendency of the tampon to permit early leakage. The tampon formed according to the preferred embodiment, FIGS. 3–6, has been tested in a conventional syngina against tampons made with the same material and in the same forming mold, but using no pretreatment of the outer portion of the fibers. The results are graphed qualitatively in FIG. 17. As the graph shows, in the early stages, the tampon of the invention has greater expansion rate, and therefore achieves an expanded size more quickly than the conventional tampon. The alignment of the X direction of the microundulated sheet (Series II, FIG. 12) in the direction in which expansion is desired, is believed to be the key to this improved expansion rate.

| 3 Gram Tampon Specimens | Improved Total Expansion and Absorption | |
| --- | --- | --- |
|  | Tampon According to the Invention | Conventional Tampon |
| Total Absorbency | 13.37 grams | 11.0 grams |
| Total Displacement | 7.27 cc | 3.8 cc |
| Per gram Absorbency (Material) | 4.34 grams | 3.70 grams |

The greater displacement of the tampon according to the invention in the above results is interpreted to confirm that improved prevention of early leakage can be achieved as a result of the invention.

The better absorbency of the above results is also a highly desirable attribute which can lead to better performance and lower cost. The improved absorption is attributed both to the improved expansion and to the superior ability of the microundulated layer (owing to the ordered closeness of the fibers) to distribute the liquid about the absorptive core, even to points remote from the point of wetting.

The improved ability to distribute liquid is very important in other respect as well. It is believed that early leakage sometimes occurs because of pooling of liquid at a local region of a tampon which effectively saturates that local region, and through movements of the wearer, enables early leakage. The microundulated exterior according to the invention causes a rapid and useful wicking action and transfer of the fluid so that undesirable pooling can be avoided.

Another desirable aspect of this transfer capability is that it enables use of core materials which, though having superior local absorption properties, lack the ability themselves to transfer fluids. By surrounding such a core with the microundulated media, the transfer to all regions of the core can be achieved without dependence upon transfer capability of the core itself.

In those tampons where the absorption capability of the microundulated material is important to the total absorption of the product, care should be taken to provide the microundulated media with the least permanance possible consistent with retaining the microundulated form while dry. This generally dictates selection of coarser undulations within the operable range and treatments in the lower part of the temperature scale. Where the absorptive capability of the microundulated material is incidental, as where the core has extreme absorption capability, a more tightly compacted microundulated media may be employed, with closer association of the microundulation fibers to maximize transfer capabilities and potential stored energy for expansion effects.

What is claimed is:

1. A tampon for absorbing menstrual discharge comprising at least one layer formed of absorbent fibers, said layer being in a prethickened, preshortened microundulated state as a result of longitudinal micro-compressive pretreatment prior to incorporation by subsequent compression into the form of said tampon, said layer being characterized by being preshortened at least 20% of its original length in the direction of pretreatment, there being at least 10 microundulations per inch in said layer in the direction of said pretreatment, adjacent microundulations in said layer residing with their sides abutting one another, with the length of a microundulation being generally of the order of the thickness of said prethickened layer, the microundulations of said layer being shape-retentive when dry with stored mechanical energy and being responsive to moisture to cause release of mechanical energy to expand in the direction of treatment of the layer to cause rapid expansion of said tampon during use.

2. The tampon of claim 1 wherein said layer is comprised of carded fibers.

3. The tampon of claim 1 wherein said tampon comprises said pretreated layer disposed about an absorptive core.

4. The tampon of claims 1, 2 or 3 wherein said layer comprises a bat folded at the head end of said tampon, the resultant multiple layers thereof being arranged to cause rapid expansion of said head upon contact with moisture.

5. The tampon of claim 1 wherein said layer comprises a bat of fibers having a weight of about 20 grams per linear meter and there are at least 25 microundulations per inch.

6. The tampon of claim 5 wherein there are about 40 microundulations per inch.

7. The tampon of claim 1 wherein said layer comprises a bat of of fibers having a weight of about 20 grams per linear meter and there are at least 20 microundulations per inch.

8. The tampon of claim 7 wherein there are about 30 microundulations per inch.

9. The tampon of claim 1 wherein said layer comprises a bat of fibers having a weight of about 30 grams per linear meter and there are at least 15 microundulations per inch.

10. The tampon of claim 9 wherein there are about 25 microundulations per inch.

11. The tampon of any of the claim 1 or 5 to 10 wherein said layer is comprised of rayon fibers.

12. The tampon of claim 1 wherein said layer comprises a bat of fibers combined prior to longitudinal compressive treatment with a thin outer layer member of hydrophilic material, said microundulations being formed in the combined assemblage.

13. The tampon of claim 1 wherein, in the completed tampon, the lines of said microundulations extend substantially parallel to the axis of said tampon, said microundulations being effective upon exposure to liquid to effect radial expansion of the outer surface of said tampon to enable interception of the menstrual discharge.

14. The tampon of claim 1 wherein, in the completed tampon, the lines of said microundulations extend at an acute angle to the axis of said tampon, said microundulations being effective upon exposure to liquid to effect expansion of said tampon with components in both the radial and the axial direction.

15. The tampon of claim 1 formed of a tampon blank having superposed layers cut originally to the same dimension including an outer layer having said microundulations and an inner layer not having said microundulations, said outer layer in said tampon being adapted and arranged, upon contact with liquid, to expand and shield cut edges of said inner layer from external contact, e.g. with walls of the vagina.

16. The tampon of claim 1 wherein said layer includes a thin nonwoven hydrophylic material.

17. The tampon of claim 1 wherein said layer includes a thin bat of substantially aligned absorbent fibers that lie substantially in the direction of said pretreatment.

18. The tampon of claim 1 wherein said layer lies in the region of the exterior of said tampon and rapid expansion thereof is effective to rapidly expand the exterior of said tampon.

19. The tampon of claim 1 formed of a tampon blank having superposed layers including an outer layer having said microundulations and an inner layer not having said microundulations.

20. A tampon for absorbing menstrual discharge comprising multiple over-lying layers of absorbent material, said layers being in a prethickened, preshortened microundulated state as a result of longitudinal microcompressive pretreatment prior to incorporation by subsequent compression into the form of said tampon, each of said layers being characterized by being preshortened at least 20% of its orignal length in the direction of pretreatment, there being at least 10 microundulations per inch in each said layer in the direction of said pretreatment, adjacent microundulations in each said layer residing with their sides abutting one another, with the length of a microundulation being generally of the order of the thickness of said prethickened layer, the microundulations of each of said layers being shape-retentive when dry with stored mechanical energy and being responsive to moisture to expand.

21. The tampon of claim 20 wherein said over-lying layers comprise successive turns of a prethickened, preshortened microundulated sheet-form member that has been rolled.

22. The tampon of claim 20 or 21 wherein said overlying layers comprise a bat of substantially aligned absorbent fibers that lie substantially in the direction of said pretreatment.

23. The tampon of claim 21 wherein the tampon is defined at its exterior by an absorbent layer that is in said prethickened, preshortened microundulated state, said layer being capable of distributing incident liquid rapidly along its extent.

24. A tampon for absorbing menstrual discharge comprising, in the region of its exterior, a layer formed of absorbent fibers, said layer being in a prethickened, preshortened microundulated state as a result of longitudinal micro-compressive pretreatment prior to incorporation by subsequent compression into the form of said tampon, said layer being characterized by being preshortened at least 20% of its original length in the direction of pretreatement, there being at least 10 microundulations per inch in said layer in the direction of said pretreatment, adjacent microundulations in said layer residing with their sides abutting one another, with the length of a microundulation being generally of the order of the thickness of said prethickened layer, the microundulations of said layer being capable of distributing liquid rapidly along its extent thereby to distribute incident liquid rapidly about said tampon, said outer layer being in liquid-transmitting relationship to absorptive material lying inwardly thereof.

25. A compressed tampon for absorbing menstrual discharge comprising a web-form bat of substantially aligned absorbent fibers, said bat being in a prethickened, preshortened microundulated state as a result of longitudinal micro-compressive pretreatment by application of compressive forces acting over a short distance substantially in the direction of the plane of the bat within the cavity of a microcreper, said bat being preshortened at least 20% of original length in a given direction aligned with the length of the fibers, to a degree permitting substantial recovery of original dimension, there being at least 10 microundulations of said bat per inch of length as a result of said pretreatment prior to incorporation in said tampon, said microundulations residing with the sides of adjacent microundulations close together as a result of said longitudinal compressive pretreatment, the absorbent fibers of said bat, because of said pretreated state, having stored mechanical energy in a predetermined selected direction within said tampon determined by the orientation of said bat within said tampon, said pretreated bat as it resides in said tampon being moisture-sensitive, responsive to small amounts of liquid to expand in said given direction due to concerted release of the stored mechanical energy in said fibers whereby rapid expansion of the exterior of said tampon can occur.

26. A compressed tampon for absorbing menstrual discharge comprising a portion of web-form bat of absorbent fibers lying along the exterior of said tampon, said bat portion being in a prethickened, preshortened microundulated state as a result of longitudinal microcompressive pretreatment by compressive forces acting over a short distance substantially in the direction of the plane of the bat within the cavity of a microcreper, said bat portion being preshortened at least 20% of original length, there being at least 10 microundulations of said bat per inch of length as a result of said pretreatment prior to incorporation in said tampon, said microundulations residing with the sides of adjacent microundulations close together as a result of said longitudinal compressive pretreatment, because of said longitudinally compressed pretreated microundulated form of said bat portion as it resides in said tampon, said bat portion having high liquid transmissivity capable of rapidly distributing liquid via said bat to portions of said tampon remote from points of incidence of said liquid upon said bat portion.

27. The tampon of claim 26 having an additonal absorbent portion different from said bat portion lying in intimate engagement therewith, said bat adapted to rapidly distribute liquid to said absorbent portion.

28. A method of producing a tampon comprising
pretreating a portion of web-form member comprised of absorbent fibers by subjecting a running length of the web-form member to longitudinal microcompressive treatment, said member being substantially confined in the direction of its faces while compressive forces in the longitudinal direction of the member are applied by a rotating drive element within the short cavity of a microcreper, said pretreatment being conducted in the manner to preshorten said web-form member at least 20% of its original length and to produce at least 10 microundulations of said member per inch of length as a result of said pretreatment, with said microundulations residing with their sides close together as a result of said longitudinal compressive pretreatment, forming a tampon preform at least in part of said pretreated web-form member, inserting said preform within a compressive tamponforming mold, and applying compression upon said preform by said mold to form said tampon.

29. The method of claim 28 wherein said web-form member comprises a portion of bat of fibers, the fibers of said bat portion during said pretreatment are substantially aligned with the longitudinal axis of said bat, and incuding the arrangement of said bat portion with repect to said perform so that in said mold the longitudinal direction of said bat portion lies substantially perpendicular to the axis of said tampon and the direction of said microundulation lines extends substantially parallel to said tampon axis, thereby to produce a tampon having a radial expansion property provided by the latent, moisture-inducable expansion of said microundulations.

30. The method of claim 28 including forming said preform by applying said microundulated web-form member to extend about an absorbent core, thereby to produce a tampon capable of rapid liquid distribution to said core due to the moisture-transmissive property of said microundulated web-form member.

31. The method of claim 30 including shaping said preform in the manner that portions of said microundulated web-form member are distributed throughout the length of said blank and the length of the resulting tampon.

32. The method of claim 31 including rolling said microundulated web into the form of a roll to serve as said preform.

33. The method of claim 32 wherein said web-form member is a bat of fibers.

* * * * *